United States Patent
Nuninger et al.

(10) Patent No.: US 6,514,959 B2
(45) Date of Patent: Feb. 4, 2003

(54) MICROBICIDES

(75) Inventors: Cosima Nuninger, Morschwiller-le-Bas (FR); John Edward Nicholas Goggin, Binningen (CH); Dino Sozzi, Sissach (CH)

(73) Assignee: Syngenta Investment Corporation, Wilmington, DE (US)

( * ) Notice: Subject to any disclaimer, the term of this patent is extended or adjusted under 35 U.S.C. 154(b) by 0 days.

(21) Appl. No.: 10/055,503

(22) Filed: Jan. 23, 2002

(65) Prior Publication Data

US 2002/0107286 A1 Aug. 8, 2002

Related U.S. Application Data

(62) Division of application No. 09/650,230, filed on Aug. 29, 2000, now Pat. No. 6,369,105, which is a division of application No. 09/573,784, filed on May 17, 2000, now Pat. No. 6,248,762, which is a division of application No. 09/365,637, filed on Aug. 3, 1999, now Pat. No. 6,087,388, which is a division of application No. 09/150,435, filed on Sep. 9, 1998, now Pat. No. 5,981,582, which is a division of application No. 08/825,285, filed on Mar. 27, 1997, now Pat. No. 5,846,571, which is a division of application No. 08/460,399, filed on Jun. 2, 1995, now Pat. No. 5,648,383.

(30) Foreign Application Priority Data

Jul. 11, 1994 (CH) .......................................... 2208/94-3

(51) Int. Cl.$^7$ ........................ A61K 31/555; A61K 31/40
(52) U.S. Cl. ...................................... 514/184; 514/417
(58) Field of Search ................................ 514/528, 184, 514/417

(56) References Cited

U.S. PATENT DOCUMENTS

4,151,299 A 4/1979 Hubele
5,601,847 A 2/1997 Bassi

FOREIGN PATENT DOCUMENTS

GB 1500581 2/1978

OTHER PUBLICATIONS

The Pesticide Manual 8th ed. 529–530, 554–555, (1991), C. Worthing, ed.
Res. Disc., 187, 632–633, Abstr. 18745 Nov. 1979.
Derwent Abstr., JP 04,365,305 (SDS Biotech Corp.).
Derwent Abst., JP 59, 027, 804 (Ishihara Sangyo Kaisha).
Abhandlungen der Akadamine dor Wissenschaften der Dor, vol. 1982 No. 1, 123–133, (1983), Schwinn et al.
C.A., vol. 102: 9129ah, (1985) Paulus et al.
The Pesticide Manual Incorp., The Agro Chemical Handbook, 10th ed. (1995) pp. 193, 194, 195.
The Pesticide Manual, 9th ed., pp. 200,207, 401 (1991), C. Worthington et al.
Libhandlungen der Akademie der Wissinschaft der DDR, vol. No. 1, (1982), (1983).

*Primary Examiner*—Alton Pryor
(74) *Attorney, Agent, or Firm*—Rose M. Allen

(57) ABSTRACT

When used in admixture with mancozeb, chlorothalonil, a copper salt, folpet, fluazinam or cymoxanil (it being possible for the latter to be used also together with one of the other five components), metalaxyl having a high R-enantiomer content of more than 70% by weight, or pure R-metalaxyl, exhibits a markedly increased fungicidal action against plant diseases as compared with a similar mixture in which metalaxyl is used in the form of the racemate.

18 Claims, No Drawings

MICROBICIDES

This application is a DIV of Ser. No. 09/650,230 filed Aug. 29, 2000 now U.S. Pat. No. 6,369,105 which is a DIV if Ser. No. 09/573,784 filed May 17, 2000 now U.S. Pat. No. 6,248,762 which is a DIV of Ser. No. 09/365,637 filed Aug. 3, 1999 now U.S. Pat. No. 6,087,388 which is a DIV of Ser. No. 09/150,435 filed Sep. 9, 1998 now U.S. Pat. No. 5,981,582 which a DIV of Ser. No. 08/825,285 filed Mar. 27, 1997 now U.S. Pat. No. 5,846,571 which is a DIV of Ser. No. 08/460,399 filed Jun. 2, 1995 now U.S. Pat. No. 5,648,383.

The present invention relates to fungicidal two- and three-component mixtures based on metalaxyl having an R-enantiomer content of more than 70% by weight, and to the use thereof in controlling and preventing Oomycetes infestation. The metalaxyl component is called active ingredient I.

The following fungicides may be used as the second component II of the mixture:

IIA) mancozeb;
IIB) chlorothalonil;
IIC) a copper salt, for example $CuCO_3$, $CuSO_4$, $Cu(OH)_2 \cdot CuCl_2$, especially $Cu(OH)_2$;
IID) folpet;
IIE) fluazinam [=3-chloro-N-(3-chloro-5-trifluoromethyl-2-pyridyl)-α,α,α-trifluoro-2,6-dinitro-p-toluidine]; and
IIF) cymoxanil, which can be used either on its own or in admixture with one of the above-mentioned components IIA to IIE (three-component mixtures).

More specifically, the invention relates to mixtures comprising metalaxyl having an R-enantiomer content of more than 85% by weight, preferably of more than 92% by weight, and especially containing pure R-enantiomer that is substantially free of S-enantiomer.

Metalaxyl of the formula

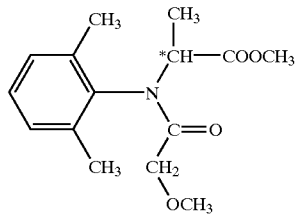

has an asymmetric *C atom and can be resolved into the enantiomers in customary manner (GB-P.1 500 581). Since 1975 it has been known to those skilled in the art that the R-enantiomer is far superior to the S-enantiomer in terms of fungicidal action and is in practice regarded as the true mechanism of action. Commercial metalaxyl is available in the form of the racemate. Likewise, mixtures of metalaxyl racemate with mancozeb, chlorothalonil, copper preparations, folpet, fluazinam or cymoxanil have become known commercially or otherwise. There has in the past never been any practical necessity to resolve the racemate, of which half consists of the desired R-enantiomer.

It has now been found, completely surprisingly, that R-metalaxyl in pure or more than 70% form, in admixture with the fungicidal components IIA to IIF, achieves a synergistically enhanced action which in some cases exceeds that of the prior-known mixtures based on the racemate by a factor of 10. Given that half of the racemate consists of R-enantiomer, factors of approximately 2 or, at most, 3 were to be expected.

With this completely unexpected result, the present invention constitutes a very considerable enrichment of the art and represents a possible means of reducing in an environmentally protective manner the total amount of fungicides used for controlling Oomycetes on plants.

In addition to the two-component mixture I:II, the present invention relates also to a method of controlling fungi, which comprises treating a site, for example a plant, that is infested by or threatened with infestation by fungi with, in any desired sequence or simultaneously, a) component I and b) the active ingredient of formula II.

Advantageous mixing ratios of the two active ingredients are I:II=from 10:1 to 1:100, preferably I:II=from 5:1 to 1:30. In many cases, mixtures in which the mixing ratio of the active substances I:II is from 1:1 to 1:20, for example 2:5, 1:4, 1:8 or 1:10, are advantageous.

The active ingredient mixtures I+II according to the invention have very advantageous curative, preventive and systemic fungicidal properties for protecting cultivated plants. The active ingredient mixtures of the invention can be used to inhibit or destroy the micro-organisms which occur on plants or on parts of plants (the fruit, blossom, leaves, stems, tubers or roots) of different crops of useful plants, while at the same time parts of plants that grow later are also protected against such microorganisms. This applies especially also to microorganisms that have developed reduced sensitivity to metalaxyl.

The active ingredient mixtures of formulae I and II are generally used in the form of compositions. R-metalaxyl (formula I) and the active ingredient of formula II can be applied to the area or plant to be treated simultaneously or in immediate succession, if desired together with further carriers, surfactants or other application-promoting adjuvants customarily employed in formulation technology.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilisers.

A preferred method of applying an active ingredient mixture comprising at least one of each of the active ingredients I and II is application to the parts of the plants that are above the soil, especially to the leaves (foliar application). The frequency and rate of application depend upon the biological and climatic living conditions of the pathogen. The active ingredients can, however, also penetrate the plant through the roots via the soil (systemic action) if the locus of the plant is impregnated with a liquid formulation or if the substances are introduced in solid form into the soil, e.g. in the form of granules (soil application).

The compounds of the combination are used in unmodified form or, preferably, together with the adjuvants conventionally employed in formulation technology, and are therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are normally from 50 g to 1800 g of active ingredient (a.i.) per hectare, preferably from 100 g to 1000 g a.i./ha. Mixtures of R-metalaxyl (I) with mancozeb (IIA) are advantageously employed at rates of application of from 100 g to 120 g of I and 1600 g of IIA.

The formulations are prepared in known manner, e.g. by homogeneously mixing and/or grinding the active ingredients with extenders, e.g. solvents, solid carriers and, where appropriate, surface-active compounds (surfactants).

The agrochemical compositions generally comprise 0.1 to 99%, preferably 0.1 to 95%, of active ingredients of formulae I and II, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

Suitable target crops are especially potatoes, vines, hops, maize, sugar beet, tobacco, vegetables (tomatoes, paprika, lettuce, etc.), and also bananas, natural rubber plants, as well as lawn areas and ornamentals. Other plants threatened by downy mildew have become known inter alia from the literature relating to metalaxyl.

The Examples which follow serve to illustrate the invention, "active ingredient" denoting a mixture of R-metalaxyl and compound II in a specific mixing ratio.

| Wettable powders | a) | b) | c) |
|---|---|---|---|
| active ingredient [I:IIA = 1:4(a), 1:16(b), 2:13(c)] | 27% | 51% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 60% | 26% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| active ingredient (I:IIA, IIB, IID or IIE = 3:7) | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Extruder granules | |
|---|---|
| active ingredient (I:IIC = 1:4) | 15% |
| sodium lignosulfonate | 2% |
| carboxymethylcellulose | 1% |
| kaolin | 82% |

The active ingredient is mixed and ground with the adjuvants, and the mixture is moistened with water. The mixture is extruded and then dried in a stream of air.

| Coated granules | |
|---|---|
| active ingredient (I:IID = 3:5) | 8% |
| polyethylene glycol (mol. wt. 200) | 3% |
| kaolin | 89% |

(mol. wt. = molecular weight)

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:IIF:IIA = 3:1:7) | 44% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% aqueous emulsion) | 1% |
| water | 28% |

The finely ground active ingredient is intimately mixed with the adjuvants, giving a suspension concentrate from which suspensions of any desired dilution can be obtained by dilution with water. Such dilutions can be used to treat living plants by spraying, pouring or immersion and to protect them against infestation by microorganisms.

BIOLOGICAL EXAMPLES

Fungicides have a synergistic effect whenever the fungicidal action of the active ingredient combination is greater than the sum of the actions of the active ingredients when applied individually.

The action E to be expected for a given active ingredient combination, for example of two fungicides, obeys the so-called COLBY formula and can be calculated as follows (COLBY, L. R. "Calculating synergistic and antagonistic responses of herbicide combinations". Weeds 15, pages 20–22, 1967) (LIMPEL et al., 1062 "Weeds control by . . . certain combinations". Proc. NEWCL, Vol. 16, pp. 48–53):

(mg a.i./liter=milligrams of active ingredient per liter or a multiple thereof)

X=% action by fungicide I at p mg a.i./liter

Y=% action by fungicide II at q mg a.i./liter

E=the expected action of fungicides I+II at a rate of application of p+q mg a.i./liter (additive action), then according to Colby:

$$E = X + Y - \frac{X \cdot Y}{100}.$$

If the action (O) actually observed is greater than the expected action, then the action of the combination is superadditive, i.e. there is a synergistic effect.

1) Action Against *Plasmopara viticola* on Vines

Small vine plants of the variety "Gutedel" are each grown in a plant-pot (diameter=6 cm) under greenhouse conditions and are sprayed in the two-leaf stage with an active ingredient mixture prepared from an emulsifiable concentrate. The following concentrations of active ingredient are each applied to four plants:

metalaxyl racemate: 2 mg and 6 mg a.i./liter;
R-metalaxyl (100%): 0.06 mg and 0.6 mg a.i./liter;
mancozeb: 2 mg and 6 mg a.i./liter.

These dilutions are prepared in demineralised water immediately before the leaves are sprayed. In order to eliminate the effect of the gas phase of the metalaxyl in the vicinity, all the plants are separated from one another laterally by means of transparent plastics films and are kept in the dark for one day at 20–22° C. and about 100% relative humidity.

The entire surface of the leaves of the plants is then uniformly sprayed to drip point with a freshly prepared sporangia suspension (120 000/ml) of a strain of *Plasmopara viticola* that is sensitive to metalaxyl. The plants are then kept at 20–22° C. and about 100% relative humidity for 7 days under artificial daylight of 16 hours' duration. Evaluation of the infestation is then carried out. The Tables show in each case the average of four parallel sprayings. The expected action in the case of mixtures is calculated according to COLBY.

Level of action of racemic metalaxyl and R-metalaxyl in admixture with residual component mancozeb

| Metalaxyl mg a.i./l | R-enantiomer of metalaxyl mg a.i./l | Mancozeb mg a.i./l | Mixing ratio | E Expected action [COLBY] | O Observed action |
|---|---|---|---|---|---|
| 2 | | | | | 12 |
| 6 | | | | | 24 |
| | 0.06 | | | | 12 |
| | 0.6 | | | | 18 |
| | | 2 | | | 0 |
| | | 6 | | | 20 |
| 2 | | 2 | 1:1 | 12 | 27 |
| 6 | | 2 | 3:1 | 24 | 71 |
| 2 | | 6 | 1:3 | 40 | 69 |
| 6 | | 6 | 1:1 | 30 | 90 |
| | 0.06 | 2 | 1:33 | 12 | 43 |
| | 0.6 | 2 | 1:3 | 18 | 56 |
| | 0.06 | 6 | 1:100 | 30 | 64 |
| | 0.6 | 6 | 1:10 | 35 | 91 | the action of 2 mg of racemic metalaxyl in admixture with 2 mg or 6 mg of mancozeb corresponds to that of 0.06 mg of R-metalaxyl in admixture with 2 mg or 6 mg of mancozeb. This shows that the action is improved about 30-fold when the R-enantiomer is used instead of racemic metalaxyl.

2) Action Against Phytophthora Infestans on Tomato Plants
Residual-protective Action After a cultivation period of 3 weeks, tomato plants are sprayed with a series of concentrations of a spray mixture prepared from an emulsifiable concentrate of the active ingredient mixture. The treated plants are infected 48 hours later with a sporangia suspension of the fungus. Fungus infestation is evaluated after incubation of the infected plants for 4 days at 90–100% relative humidity and 20° C.

The following results are obtained:

| Mancozeb [ppm a.i.] | Metalaxyl [ppm a.i.] | R-enantiomer of metalaxyl [ppm a.i.] | Percent action |
|---|---|---|---|
| 20 | 2 | | 18 |
| 6 | 0.6 | | 0 |
| 20 | | 2 | 75 |
| 6 | | 0.6 | 7 |

| Copper oxychloride [ppm a.i.] | Metalaxyl [ppm a.i.] | R-enantiomer of metalaxyl [ppm a.i.] | Percent action |
|---|---|---|---|
| 60 | 6 | | 35 |
| 60 | 2 | | 17.5 |
| 60 | | 6 | 75 |
| 60 | | 2 | 50 |

3) Action Against Phytophthora on Potato Plants
Residual-protective Action

After cultivation period of 3 weeks, 2- to 3-week-old potato plants (variety Bintje) are sprayed with a series of concentrations of a spray mixture prepared from an emulsifiable concentrate of the active ingredient mixture. The treated plants are infected 24 hours later with a sporangia suspension of the fungus. Fungus infestation is evaluated after incubation of the infected plants for 5 days at 90–100% relative humidity and 20° C.

The following results are obtained:

| Mancozeb [ppm a.i.] | Metalaxyl [ppm a.i.] | R-enantiomer of metalaxyl [ppm a.i.] | Percent action |
|---|---|---|---|
| 20 | 2 | | 70 |
| 6 | 0.6 | | 15 |
| 20 | | 2 | 100 |
| 6 | | 0.6 | 50 |

| Copper oxychloride [ppm a.i.] | Metalaxyl [ppm a.i.] | R-enantiomer of metalaxyl [ppm a.i.] | Percent action |
|---|---|---|---|
| 60 | 6 | | 17.5 |
| 60 | 2 | | 0 |
| 60 | | 6 | 70 |
| 60 | | 2 | 35 |

Similarly markedly increased actions are achieved also with the other components IIB, IID, IIE and IIF of the mixture.

Preferred mixing ratios (in amounts by weight) are:
R-metalaxyl(I):IIA (mancozeb)=1:1 to 1:20
I:IIB (chlorothalonil)=2:1 to 1:12
I:IIC (copper preparation)=5:1 to 1:30
I:IID (folpet)=3:1 to 1:10
I:IIE (fluazinam)=5:1 to 1:20
I:IIF (cymoxanil)=6:1 to 1:6
I:IIF:IIA=1 to 7:1:4 to 10
I:IIF:IID=1 to 7:1:2 to 8.

These marked increases in action with R-metalaxyl are observed also against other Oomycetes, especially Peronosporales, Pseudoperonospora, *Albugo occidentalis*, Phytophthora spp., Pythium, Bremia and other pathogens.

What is claimed is:

1. A fungicidal composition comprising fungicidally effective amounts of (I) metalaxyl, wherein more than 70% by weight of the metalaxyl is the R-enantiomer (IIF), cymoxanil, and a third component (IIA) mancozeb, wherein the ratios by weight of I:IIF:IIA=1 to 7:1:4 to 10, and an inert carrier is synergistic.

2. A composition of claim 1, wherein the metalaxyl has an R-enantiomer content of more than 85% by weight.

3. A composition of claim 1, wherein the metalaxyl has an R-enantiomer content of more than 92% by weight.

4. A composition of claim 1, wherein the metalaxyl is substantially free of the S-enantiomer.

5. A method of controlling and preventing Oomycetes infestation in plants, parts of plants, or at the site of their growth, which comprises applying thereto a synergistic, fungicidally effective amounts in any desired sequence, simultaneously or in immediate succession, (I) metalaxyl, wherein more than 70% by weight is the R-enantiomer, (IIF) cymoxanil, and a third component (IIA) mancozeb, wherein the ratios by weight of I:IIF:IIA=1 to 7:1:1 to 10.

6. A method of claim 5, wherein the metalaxyl has an R-enantiomer content of more than 85% by weight.

7. A method of claim 5, wherein the metalaxyl has an R-enantiomer content of more than 92% by weight.

8. A method of claim 5, wherein the R-metalaxyl is substantially free of the S-enantiomer.

9. A method of claim 5, wherein the plants are selected from Phytophthora spp., Plasmopara, Pythium, Pseudoperonospora, Albugo occidentials, and Bremia.

10. A fungicidal composition comprising fungicidally effective amounts of (I) metalaxyl, wherein more than 70% by weight of the metalaxyl is the R-enantiomer (IIF), cymoxanil, and a third component (IID) folpet, wherein the ratios by weight of I:IIF:IID=1 to 7:1:2 to 8, and an inert carrier is synergistic.

11. A composition of claim 10, wherein the metalaxyl has an R-enantiomer content of more than 85% by weight.

12. A composition of claim 10, wherein the metalaxyl has an R-enantiomer content of more than 92% by weight.

13. A composition of claim 10, wherein the metalaxyl is substantially free of the S-enantiomer.

14. A method of controlling and preventing Oomycetes infestation in plants, parts of plants, or at the site of their growth, which comprises applying thereto a synergistic, fungicidally effective amounts in any desired sequence, simultaneously or in immediate succession, (I) metalaxyl, wherein more than 70% by weight is the R-enantiomer, (IFF) cymoxanil, and a third component (IID) folpet, wherein the ratios by weight of I:IIF:IID=1 to 7:1:2 to 8.

15. A method of claim 14, wherein the metalaxyl has an R-enantiomer content of more than 85% by weight.

16. A method of claim 14, wherein the metalaxyl has an R-enantiomer content of more than 92% by weight.

17. A method of claim 14, wherein the R-metalaxyl is substantially free of the S-enantiomer.

18. A method of claim 14, wherein the plants are selected from Phytophthora spp., Plasmopara, Pythium, Pseudoperonospora, Albugo occidentials, and Bremia.

* * * * *